(12) United States Patent
Yamamura et al.

(10) Patent No.: US 10,603,061 B2
(45) Date of Patent: Mar. 31, 2020

(54) FORCEPS DEVICE AND SURGICAL SYSTEM

(71) Applicant: OLYMPUS CORPORATION, Tokyo (JP)

(72) Inventors: Nahoko Yamamura, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 458 days.

(21) Appl. No.: 15/377,136

(22) Filed: Dec. 13, 2016

(65) Prior Publication Data

US 2017/0086870 A1 Mar. 30, 2017

Related U.S. Application Data

(63) Continuation of application No. PCT/JP2015/065946, filed on Jun. 2, 2015.

(30) Foreign Application Priority Data

Jun. 19, 2014 (JP) .................................. 2014-126229

(51) Int. Cl.
*A61B 18/14* (2006.01)
*A61B 17/29* (2006.01)
(Continued)

(52) U.S. Cl.
CPC .......... *A61B 17/29* (2013.01); *A61B 1/00133* (2013.01); *A61B 1/018* (2013.01);
(Continued)

(58) Field of Classification Search
CPC ....... A61B 17/28; A61B 17/29; A61B 18/085; A61B 18/12; A61B 1/00098;
(Continued)

(56) References Cited

U.S. PATENT DOCUMENTS 5,133,735 A * 7/1992 Slater ................. A61B 17/2909
606/205
6,241,723 B1 * 6/2001 Heim ..................... A61B 18/12
606/32
(Continued)

FOREIGN PATENT DOCUMENTS

| EP | 2 123 210 A1 | 11/2009 |
|---|---|---|
| EP | 2 123 225 A1 | 11/2009 |
| EP | 2 478 860 A1 | 7/2012 |
| JP | 2004-57588 A | 2/2004 |
| JP | 2008-194302 A | 8/2008 |
| JP | 2009-279411 A | 12/2009 |
| JP | 4804871 B2 | 11/2011 |

(Continued)

OTHER PUBLICATIONS

International Search Report dated Sep. 1, 2015 received in International Application No. PCT/JP2015/065946.
(Continued)

*Primary Examiner* — Michael F Peffley
*Assistant Examiner* — Amanda L Zink
(74) *Attorney, Agent, or Firm* — Scully, Scott, Murphy & Presser, P.C.

(57) ABSTRACT

Provided is a forceps device including: an elongated body portion; a pair of gripping pieces that are provided at a distal end of the body portion, at least one of which possesses conductivity; a motive-power output portion that is provided at a base end of the body portion; a motive-power converting mechanism that connects the pair of gripping pieces and the motive-power output portion, and that converts motive power output by the motive-power output portion into relative opening/closing motions of the pair of gripping pieces; and an insulating member that is provided in a pathway connecting the pair of gripping pieces and the motive-power output portion via the motive-power converting mechanism.

16 Claims, 12 Drawing Sheets

(51) Int. Cl.
*A61B 1/00* (2006.01)
*A61B 1/018* (2006.01)
*A61B 18/08* (2006.01)
*A61B 18/00* (2006.01)
*A61B 90/00* (2016.01)
*A61B 17/00* (2006.01)

(52) U.S. Cl.
CPC ........ *A61B 18/085* (2013.01); *A61B 18/1442* (2013.01); *A61B 18/1492* (2013.01); *A61B 1/00098* (2013.01); *A61B 2017/003* (2013.01); *A61B 2017/00398* (2013.01); *A61B 2017/2903* (2013.01); *A61B 2018/00077* (2013.01); *A61B 2018/00083* (2013.01); *A61B 2018/00178* (2013.01); *A61B 2018/00589* (2013.01); *A61B 2018/00601* (2013.01); *A61B 2018/00982* (2013.01); *A61B 2018/1405* (2013.01); *A61B 2090/065* (2016.02)

(58) Field of Classification Search
CPC ................ A61B 1/00133; A61B 1/018; A61B 2017/00398; A61B 2017/2903; A61B 2018/00589
See application file for complete search history.

(56) References Cited

U.S. PATENT DOCUMENTS

| | | |
|---|---|---|
| 2003/0216733 A1* | 11/2003 | McClurken ............ A61B 18/14 606/51 |
| 2004/0073210 A1 | 4/2004 | Taniguchi et al. |
| 2005/0010212 A1 | 1/2005 | McClurken et al. |
| 2005/0113827 A1 | 5/2005 | Dumbauld et al. |
| 2006/0116675 A1 | 6/2006 | McClurken et al. |
| 2008/0194910 A1 | 8/2008 | Miyamato et al. |
| 2009/0292164 A1 | 11/2009 | Yamatani |
| 2009/0299136 A1* | 12/2009 | Hasegawa ............ A61B 1/0051 600/106 |
| 2012/0136424 A1 | 5/2012 | Kimura et al. |
| 2015/0335388 A1 | 11/2015 | Iida et al. |

FOREIGN PATENT DOCUMENTS

| | | |
|---|---|---|
| JP | 5042700 B2 | 10/2012 |
| WO | 03/096880 A2 | 11/2003 |
| WO | 2009/016834 A1 | 2/2009 |
| WO | 2014/084409 A1 | 6/2014 |

OTHER PUBLICATIONS

Extended Supplementary European Search Report dated Jan. 16, 2018 in European Patent Application No. 15 80 9916.8.

* cited by examiner

FORCEPS DEVICE AND SURGICAL SYSTEM

CROSS-REFERENCE TO RELATED APPLICATIONS

This is a continuation of International Application PCT/JP2015/065946, with an international filing date of Jun. 2, 2015, which is hereby incorporated by reference herein in its entirety. This application claims the benefit of Japanese Patent Application No. 2014-126229, the content of which is incorporated herein by reference.

TECHNICAL FIELD

The present invention relates to a forceps device and a surgical system.

BACKGROUND ART

In the related art, there are known gripping forceps that are provided with: a pair of gripping pieces; a cylindrical sheath in which the pair of gripping pieces at the distal end thereof; a driving system provided at the base end of the sheath; and manipulation wires that connect the gripping pieces and the driving system and that open/close the pair of gripping pieces by manually or electrically pushing and pulling the manipulation wires by means of the driving system (for example, see Patent Literature 1).

On the other hand, in a method that is generally used during surgery, as a simple hemostatic method, a bleeding point is pinched by using metal tweezers, and an electric scalpel is brought into contact with the tweezers to supply a high-frequency current to the tweezers from the electric scalpel, thus coagulating tissue around the bleeding point by means of heat.

CITATION LIST

Patent Literature

{PTL 1} Publication of Japanese Patent No. 5042700

SUMMARY OF INVENTION

Technical Problem

A first aspect of the present invention is a forceps device including: an elongated body portion; a pair of gripping pieces that are provided at a distal end of the body portion, at least one of which possesses conductivity, and that can be opened/closed relative to each other; a motive-power output portion that is provided at a base end of the body portion and that outputs motive power; a motive-power converting mechanism that connects the pair of gripping pieces and the motive-power output portion, and that converts the motive power output by the motive-power output portion into relative opening/closing motions of the pair of gripping pieces; and an insulating member that is provided in a pathway connecting the pair of gripping pieces and the motive-power output portion via the motive-power converting mechanism, and that electrically insulates the pair of gripping pieces and the motive-power output portion from each other.

A second aspect of the present invention is a surgical system including: any one of forceps devices described above; a high-frequency treatment device that includes an elongated body portion, and an electrode provided at a distal end of the body portion, and that discharges a high-frequency current; an endoscope that has two treatment-tool channels into which the forceps device and the high-frequency treatment device are individually inserted; and a contact part for placing the pair of gripping pieces and the electrode, which protrude from a distal-end surface of the endoscope via the treatment-tool channels, at positions at which mutual electrical connections are established therebetween.

DESCRIPTION OF EMBODIMENT

A forceps device 1 and a high-frequency treatment device 2, as well as a surgical system 100 provided with them, according to an embodiment of the present invention will be described below with reference to the drawings.

Figure 1:
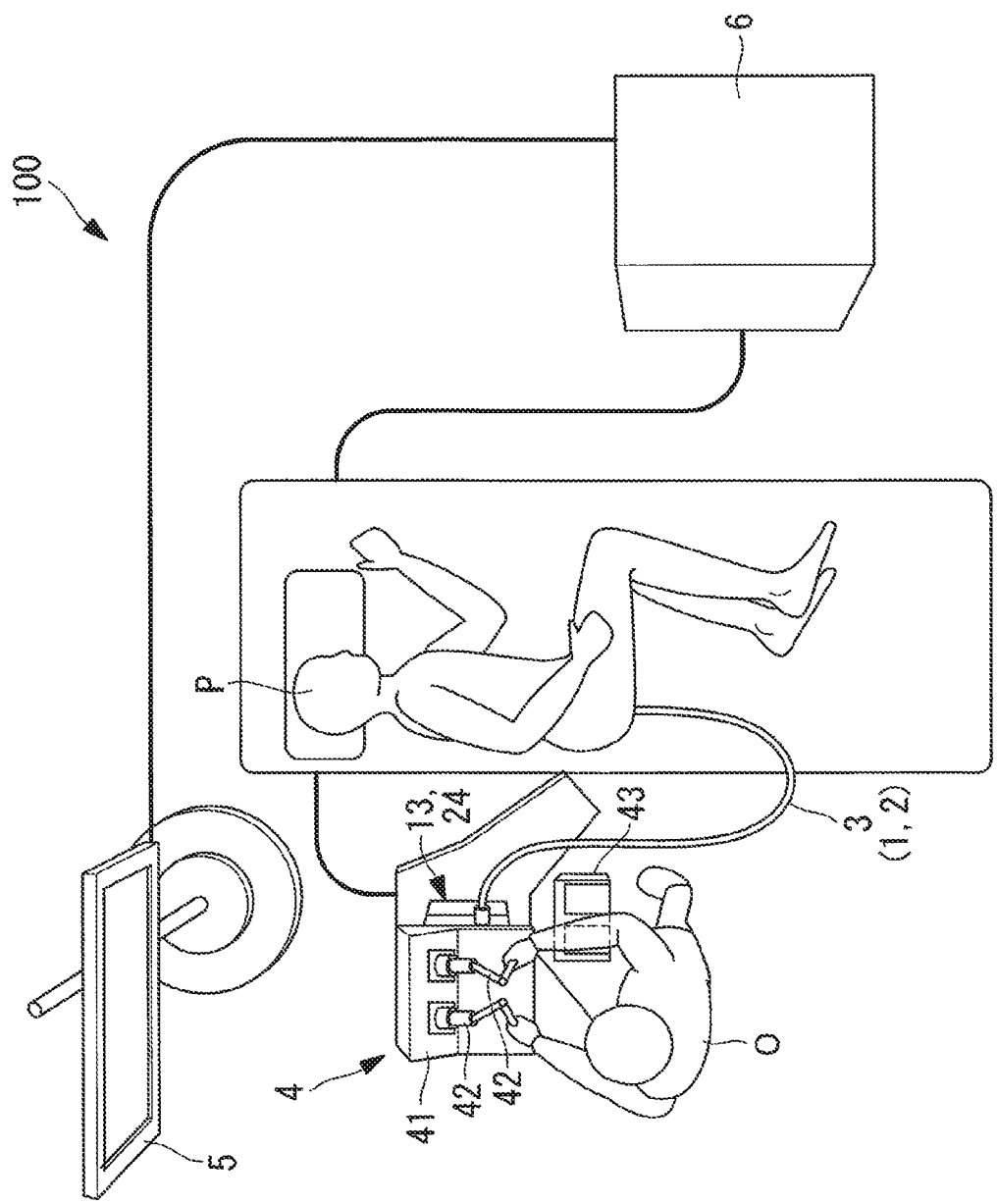
FIG. 1 is an overall configuration diagram of a surgical system according to an embodiment of the present invention.

In the surgical system 100 shown in FIG. 1, the forceps device 1 and the high-frequency treatment device 2 according to this embodiment pass through the interior of an endoscope 3, and thus, are inserted into the body of a patient P.

As shown in FIG. 1, the surgical system 100 is provided with: the flexible endoscope 3 that is inserted into the body; a manipulation input device 4 that is manipulated by an operator O, such as a surgeon or the like; a display portion 5 that displays an image acquired by using the endoscope 3; and a control portion 6 that controls the forceps device 1 and the high-frequency treatment device 2 in accordance with manipulations input via the manipulation input device 4.

The endoscope 3 has treatment-tool channels that are formed so as to pass through the endoscope 3 in a longitudinal direction and into which body portions 11 and 21 (described later) of the forceps device 1 and the high-frequency treatment device 2 can individually be inserted.

The manipulation input device 4 includes: a manipulation table 41; manipulation arms 42 that are attached to the manipulation table 41; and foot switches 43. The manipulation input device 4 transmits input signals in accordance with the manipulations input by using the manipulation arms 42 and the foot switches 43 to the control portion 6.

The control portion 6 is configured so as to electrically control the forceps device 1 and the high-frequency treatment device 2 in accordance with the input signals transmitted thereto from the manipulation input device 4.

Figure 2:
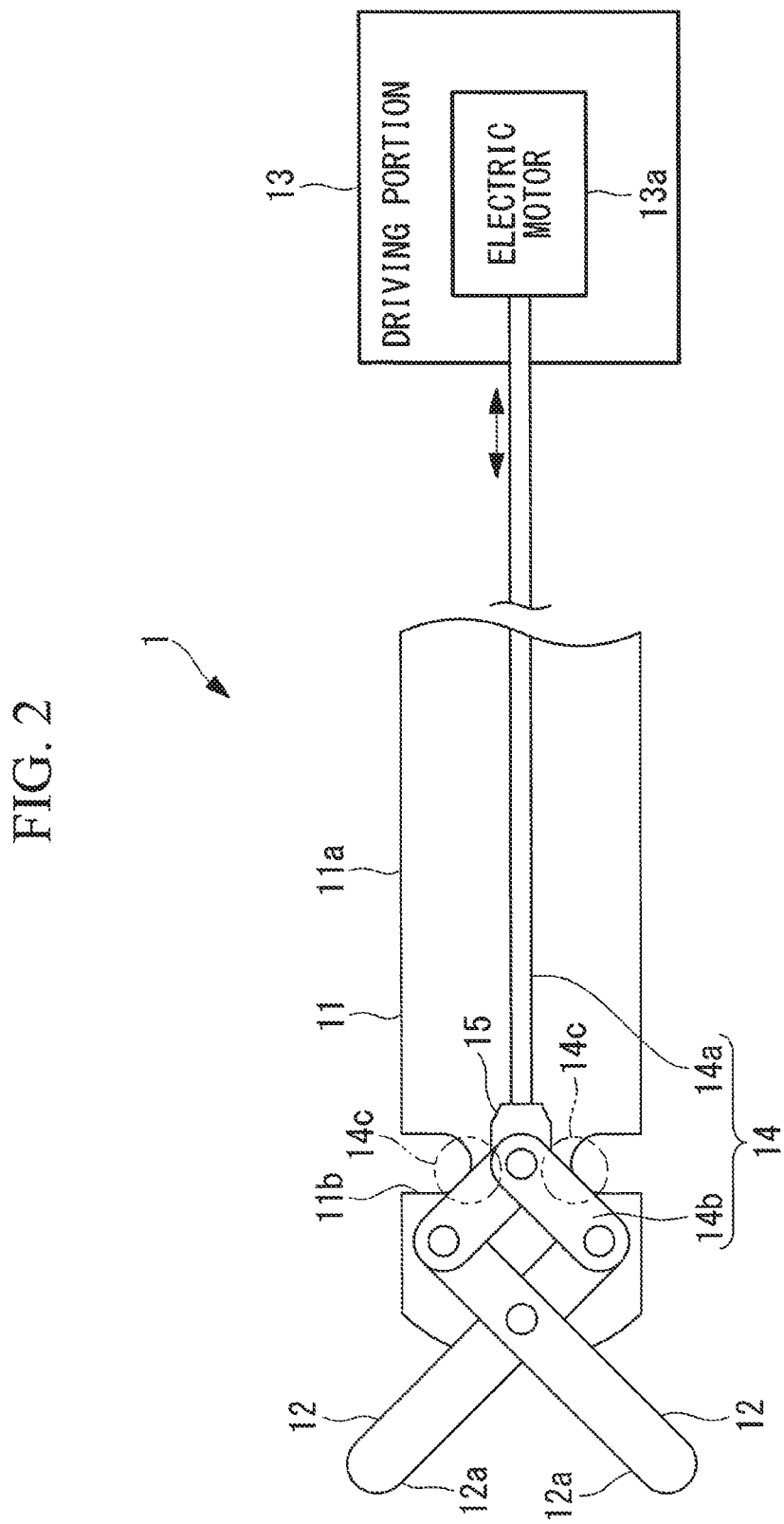
FIG. 2 is an overall configuration diagram of a forceps device provided in the surgical system in FIG. 1.

As shown in FIG. 2, the forceps device 1 according to this embodiment is provided with: a forceps main unit having an elongated body portion 11 and a pair of gripping pieces 12 that are provided at the distal end of the body portion 11; a driving portion 13 that is connected to the base end of the body portion 11 and that has an electric motor (motive-power output portion) 13a that outputs a motive power in accordance with the control signals transmitted thereto from the control portion 6; and a motive-power converting mechanism 14 and an insulating member 15 that are provided inside the body portion 11.

The body portion 11 has a cylindrical sheath 11a that includes the motive-power converting mechanism 14 and the insulating member 15 as built-in components. The sheath 11a possesses electrical insulating properties, thus serving as electrical insulation between the interior and the exterior of the body portion 11. The sheath 11a has, in a side wall thereof, a slit 11b that is formed so as to pass through the side wall in the wall-thickness direction. The slit 11b is formed at a position corresponding to that of a portion 14c of a linkage mechanism 14b, described later, and thus, the portion of the linkage mechanism 14b is exposed outside the sheath 11a via the slit 11b. The exposed portion 14c of the linkage mechanism 14b forms an electric contact portion that serves as an electric contact point between the gripping pieces 12 and an electrode 22 (described later) of the high-frequency treatment device 2. In the following, this portion 14c will also be referred to as an electric contact portion.

The pair of gripping pieces 12 individually have gripping surfaces 12a, and the gripping surfaces 12a are disposed so as to face each other.

The motive-power converting mechanism 14 is provided with: a manipulation wire 14a that extends along the longitudinal axis of the body portion 11; and the linkage mechanism 14b that is provided on the distal-end side of the manipulation wire 14a and that is coupled with base ends of the gripping pieces 12. The manipulation wire 14a and the linkage mechanism 14b are coupled with each other via the insulating member 15 provided therebetween. The manipulation wire 14a is connected, at the base end thereof, to the electric motor 13a inside the driving portion 13 and is configured so as to be linearly moved in the longitudinal direction due to the motive power output by the electric motor 13a. The linkage mechanism 14b is configured so as to convert the linear motion transmitted to the base end thereof from the manipulation wire 14a via the insulating member 15 into opening/closing motions of the pair of gripping pieces 12.

The pair of gripping pieces 12, the manipulation wire 14a, and the linkage mechanism 14b are formed of a metal, such as stainless steel, titanium, tungsten, or the like, and possess conductivity.

Note that, FIG. 2 shows the linkage mechanism 14b that is connected to the base ends of both gripping pieces, and that is configured so as to perform the opening/closing motions of the pair of gripping pieces 12 by simultaneously moving, in a pivoting manner, both gripping pieces 12 about axes that intersect the longitudinal axis of the body portion 11; however, alternatively, it is permissible to employ a linkage mechanism that is connected only to the base end of one of the gripping pieces 12, and that is configured so as, by moving only this gripping piece 12 in a pivoting manner, to perform opening/closing motions of the gripping piece 12 relative to the other gripping piece 12.

The insulating member 15 possesses electrical insulating properties and serves as electrical insulation between the linkage mechanism 14b and the manipulation wire 14a. As the material for the insulating member 15, polyether ether ketone (PEEK), ceramic, polytetrafluoroethylene (PTFE), polycarbonate, or the like is used. A non-polar plastic, such as PTFE or the like, which has a lower dissipation factor, is more preferable because, as will be described later, it is possible to prevent deformation of the insulating member 15 due to an increase in temperature by suppressing dielectric heating of the insulating member 15 when a high-frequency current is supplied to the gripping pieces 12.

As the insulating member 15, it is permissible to use a member that is formed by covering an outer surface of a main unit made of a conductor with an insulator. As the insulator to be used in this case, a silicone resin, PTFE, white alumina (high-purity aluminum oxide) or the like is preferable.

Figure 3:
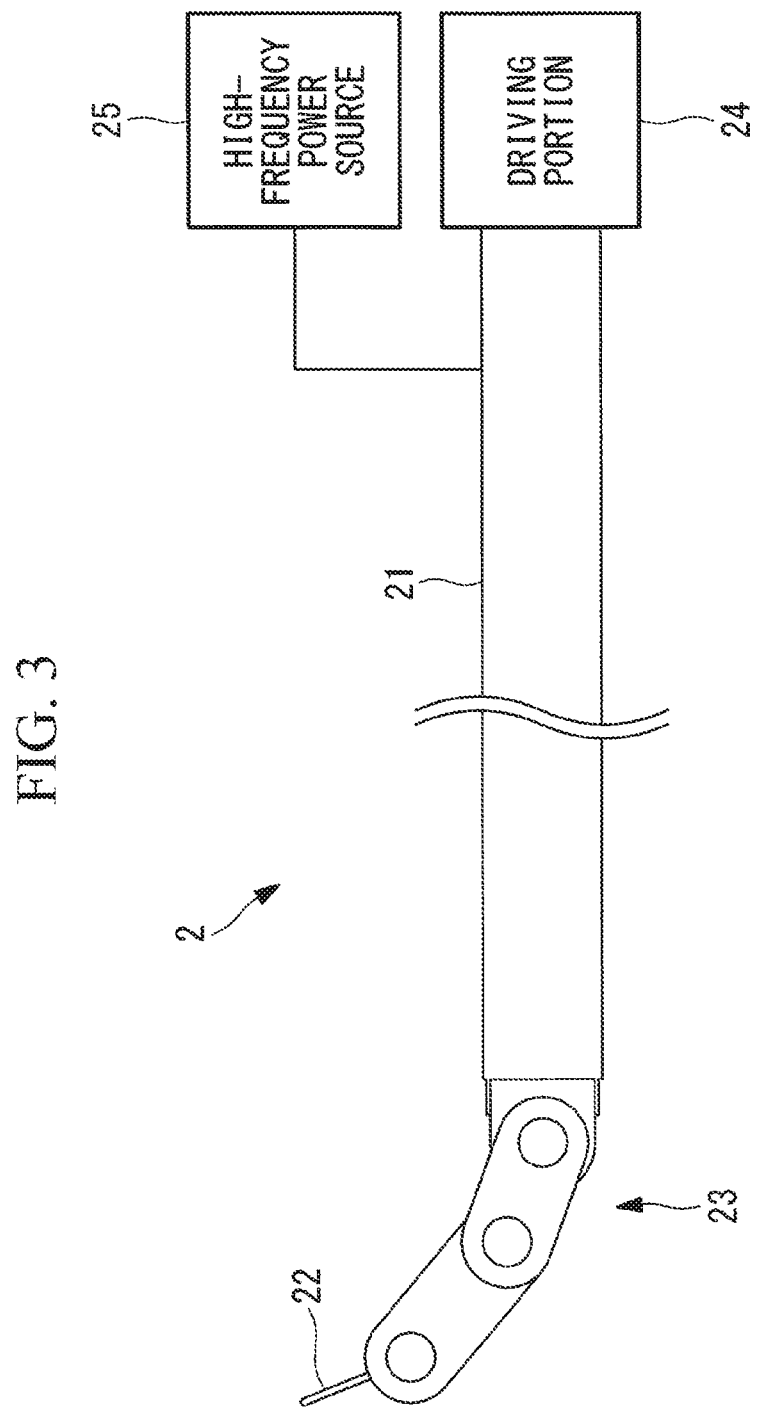
FIG. 3 is an overall configuration diagram of a high-frequency treatment device provided in the surgical system in FIG. 1.

As shown in FIG. 3, the high-frequency treatment device 2 according to this embodiment is provided with: an elongated body portion 21; the single rod-shaped electrode 22 that is positioned on the distal-end side of the body portion 21; an electric-scalpel main unit having a joint portion (contact part) 23 that couples the body portion 21 and the electrode 22; a driving portion 24 that is connected to the base end of the body portion 21 and that electrically drives the joint portion 23; and a high-frequency power source 25 that supplies a high-frequency current to the electrode 22 via the interiors of the body portion 21 and the joint portion 23.

Figure 4:
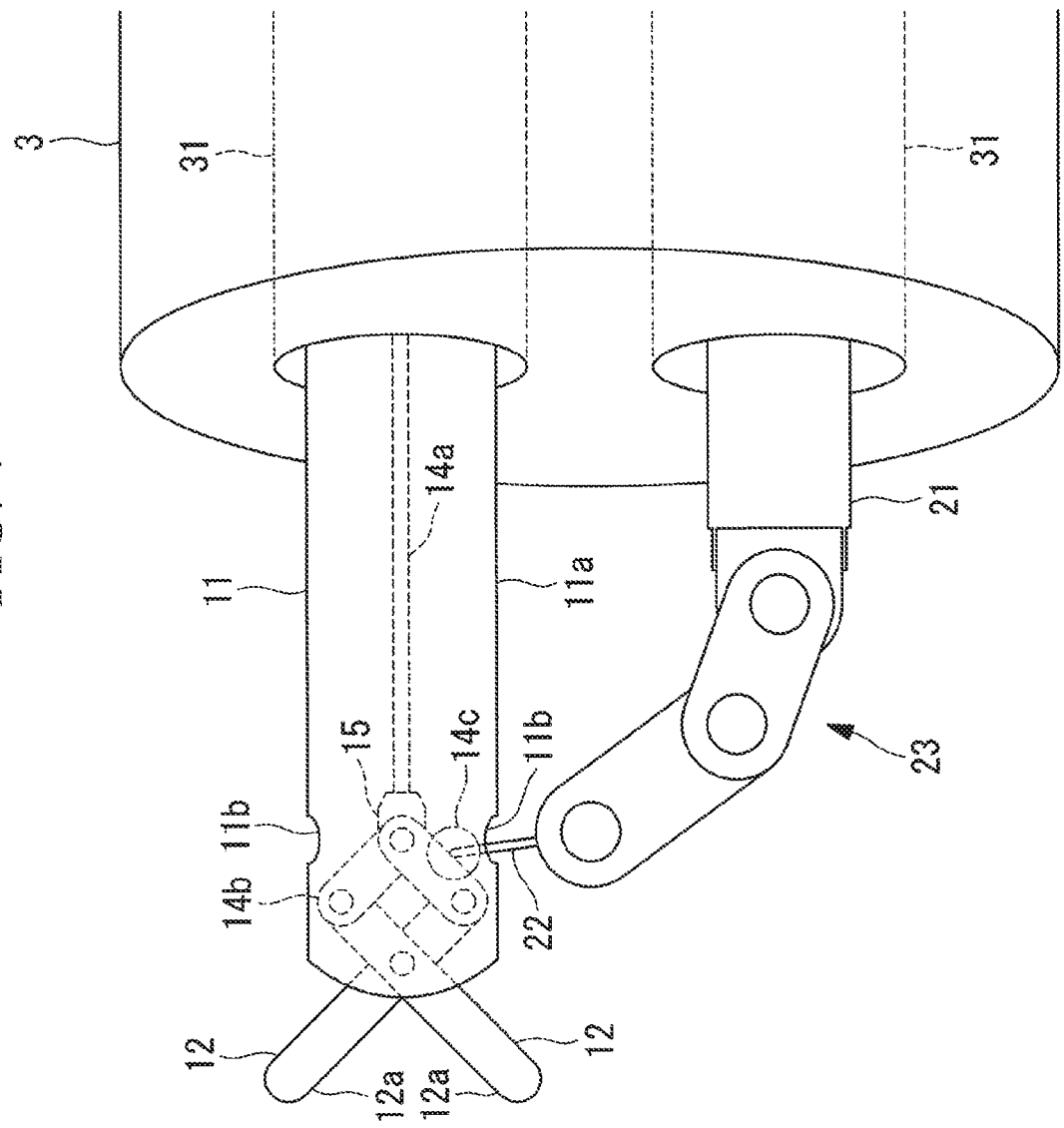
FIG. 4 is a diagram for explaining motions of the forceps device and the high-frequency treatment device in the case in which the forceps device is used as high-frequency hemostatic forceps.

The joint portion 23 can be flexed about an axis that intersects the longitudinal axis of the body portion 21. Here, as shown in FIG. 4, the flexing direction and the flexing angle of the joint portion 23 are designed so that the electrode 22 can be brought into contact with an outer surface of the gripping pieces 12 or the electric contact portion 14c via the slit 11b in a state in which the gripping pieces 12 of the forceps device 1 and the electrode 22 of the high-frequency treatment device 2 are disposed so as to protrude from treatment-tool channels 31 whose openings are at the distal-end surface of the endoscope 3.

Next, the operation of the thus-configured surgical system 100 will be described.

The body portions 11 and 21 of the forceps device 1 and the high-frequency treatment device 2 are inserted into the large intestine of a patient P resting on a bed via the treatment-tool channels 31 of the endoscope 3 inserted into the large intestine from his/her anus.

Figure 5:
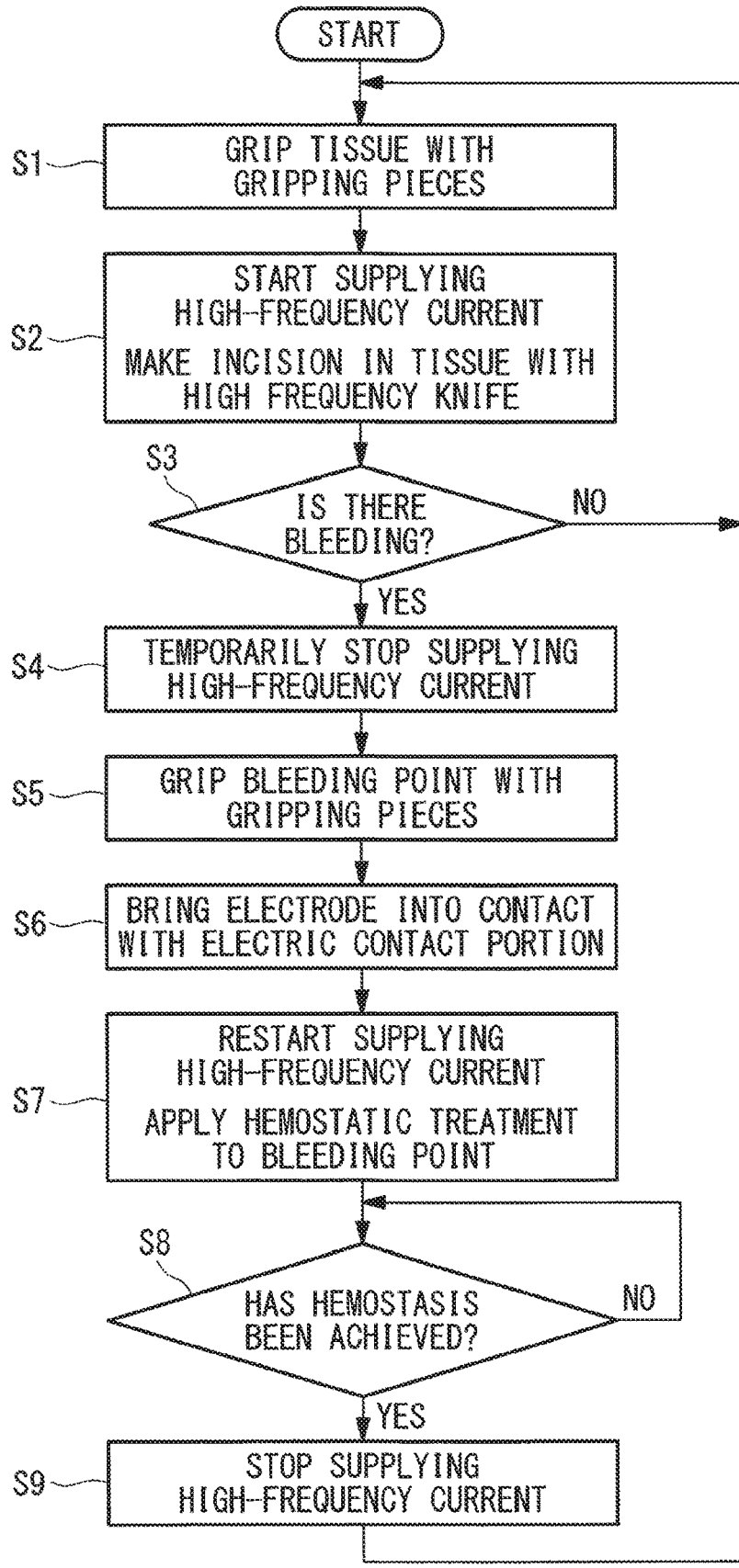
FIG. 5 is a flowchart showing a surgical method employing the surgical system in FIG. 1.

FIG. 5 is a flowchart showing procedures of a surgical method in which the surgical system 100 is used. The operator O manipulates the manipulation input device 4 and actuates the forceps device 1 and the high-frequency treatment device 2 in the large intestine, thus executing the following procedures.

First, tissue in the vicinity of a site to be treated is gripped between the pair of gripping pieces 12, and the gripped tissue is pulled, thus imparting a tensile force to the tissue in the site to be treated (step S1). Next, the high-frequency power source 25 starts to supply a high-frequency current to the electrode 22, and an incision is made at the site to be treated by using the electrode 22 (step S2).

In the case in which the tissue starts to bleed while making the incision ("YES" in step S3), the supply of the high-frequency current is temporarily stopped (step S4), and the bleeding point is gripped by using the pair of gripping pieces 12 (step S5). Next, the joint portion 23 of the high-frequency treatment device 2 is manipulated to bring the electrode 22 into contact with the electric contact portion 14c (step S6), thus restarting the supply of the high-frequency current (step S7). By doing so, the high-frequency current is supplied to the pair of gripping pieces 12 that are electrically connected to the electrode 22, and, because the tissue around the bleeding point being gripped by the pair of gripping pieces 12 becomes coagulated by heat due to the high-frequency current, it is possible to achieve hemostasis thereof.

Continuous waves of the high-frequency current are suitable for making an incision, and intermittent waves of the high-frequency current are suitable for performing a hemostatic treatment. Therefore, the output setting of the high-frequency power source 25 may be changed in steps S2 and S7, as appropriate. After hemostasis is achieved ("YES" in step S8), the supply of the high-frequency current is stopped (step S9), and the procedure to make the incision is continued (step S1).

In this case, with this embodiment, the insulating member 15 that is provided in the pathway connecting the pair of gripping pieces 12 and the electric motor 13a electrically insulates the electric motor 13a from the pair of gripping pieces 12. Therefore, the high-frequency current supplied to the pair of gripping pieces 12 does not flow into the electric motor 13a nor the manipulation input device 4 and the control portion 6 that are electrically connected to the electric motor 13a, and thus, the high-frequency current does not affect the electrical systems of the surgical system 100. In addition, electrical systems of peripheral devices that are used together with the forceps device 1, such as an endoscope or the like into which the forceps device 1 is inserted, are also prevented from being affected by noise or the like. Therefore, there is an advantage in that it is possible to suitably utilize the forceps device 1 as an energy treatment tool, in particular, as high-frequency hemostatic forceps.

In addition, the slit 11b is provided at an intermediate position in the longitudinal direction of the sheath 11a and the electric contact portion 14c that is electrically connected to the gripping pieces 12 is provided farther on the base-end side, and thus, there is an advantage in that manipulations for supplying the high-frequency current, by bringing the electrode 22 into contact with the gripping pieces 12, can easily be performed at a position farther away from the tissue being gripped by the gripping pieces 12. In addition, by providing the electric contact portion 14c inside the sheath 11b, the electrode 22 that is in contact with the electric contact portion 14c is accommodated in the sheath 11a in that state. Therefore, there is an advantage in that it is possible to more reliably prevent contact with the tissue around the electrode 22. Furthermore, because the position of the electrode 22 with respect to the electric contact portion 14c is stabilized in a state in which the electrode 22 is inserted into the slit 11b, there is an advantage in that it is possible to stably maintain the connection between the electrode 22 and the electric contact portion 14c.

Figure 6A:
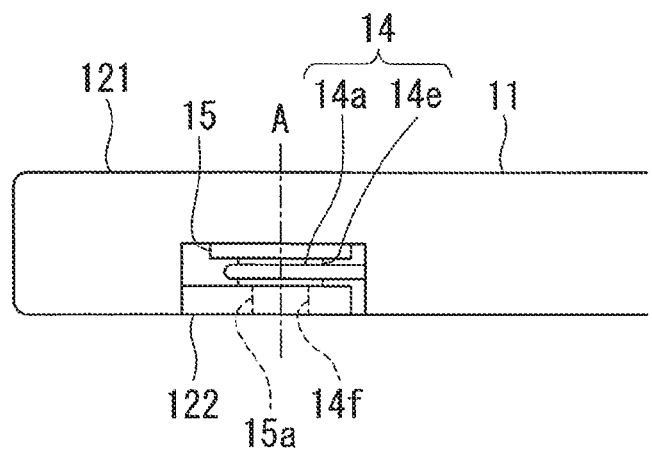
FIG. 6A is a partial plan view showing a modification of the forceps device in FIG. 2.
Figure 6B:
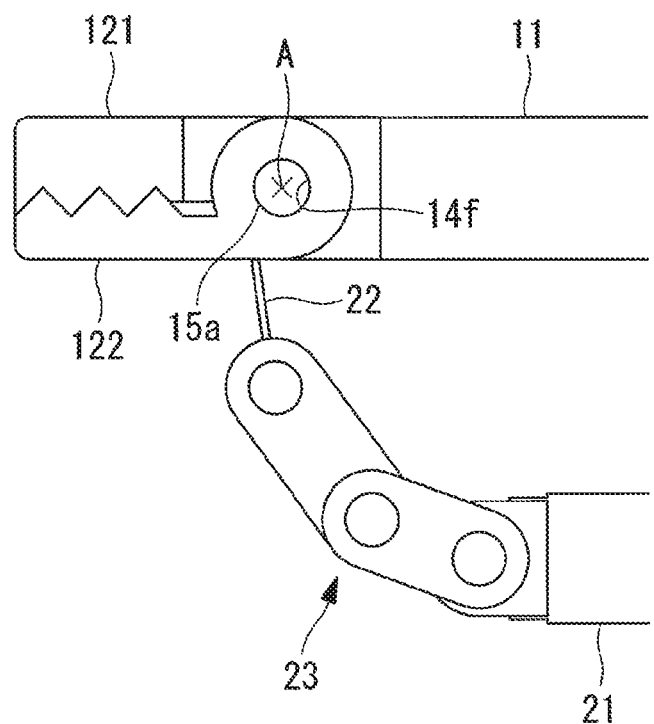
FIG. 6B is a side view of the forceps device in FIG. 6A.

Note that, in this embodiment, although the pair of gripping pieces 12 both possess conductivity, alternatively, as shown in FIGS. 6A and 6B, a first gripping piece 121 may possess conductivity, and a second gripping piece 122 may be formed of an electric insulator. In this case, the motive-power converting mechanism 14 is connected only to the second gripping piece 122, and the motive-power converting mechanism 14 connected to the second gripping piece 122 is coupled with the first gripping piece 121. In other words, the second gripping piece 122 also serves as an insulating member. Furthermore, the first gripping piece 121 and the second gripping piece 122 are coupled with each other via the insulating member 15.

Specifically, in FIGS. 6A and 6B, a combination of the manipulation wire 14a and a pulley 14e is employed as the motive-power converting mechanism 14, instead of the combination of the manipulation wire 14a and the linkage mechanism 14b. The pulley 14e is formed as a portion of the second gripping piece 122 at a base end of the second gripping piece 122 of the pair of gripping pieces 121 and 122, and the pulley 14e has a hole 14f on the center axis thereof. The insulating member 15 is formed as a portion of the first gripping piece 121 at a base end of the first gripping piece 121, and the insulating member 15 is provided with a protrusion 15a that extends in a direction that is orthogonal to the longitudinal axis of the body portion 11. When the protrusion 15a is inserted into the hole 14f of the pulley 14e, the second gripping piece 122 is coupled with the first gripping piece 121 so as to be rotatable about a pivoting axis A that is orthogonal to the longitudinal axis of the body portion 11. The manipulation wire 14a is connected to the pulley 14e so as to, by means of the linear motion thereof, alternatively impart rotational motions in clockwise and counterclockwise directions to the pulley 14e, and the rotations of the pulley 14e cause the second gripping piece 122 to undergo opening/closing motions relative to the gripping piece 121, which is the first gripping piece in the pair.

By doing so, when gripping tissue, by placing the second gripping piece 122 formed of an electric insulator on a side that is adjacent to the tissue, it is possible to protect the tissue around the bleeding point from the high-frequency current.

Note that, in the second gripping piece 122, only an outer surface exposed to the tissue may be covered with an electric insulator, instead of forming the entirety thereof by using an electric insulator. By doing so also, it is possible to protect the peripheral tissue from the high-frequency current supplied to the first gripping piece 121. In this case, it is necessary to provide an insulating member other than the second gripping piece 122, like the insulating member 15 interposed between the first gripping piece 121 and the second gripping piece 122.

In the case in which the combination of the manipulation wire 14a and the pulley 14e is employed as the motive-power converting mechanism 14, the pulley 14e may be provided for each of the gripping pieces 121 and 122 at the respective base ends thereof, and the motive-power converting mechanism 14 may be configured so as to cause both gripping pieces 121 and 122 to undergo opening/closing motions by simultaneously rotating the two pulleys 14e in directions opposite from each other.

Figure 7:
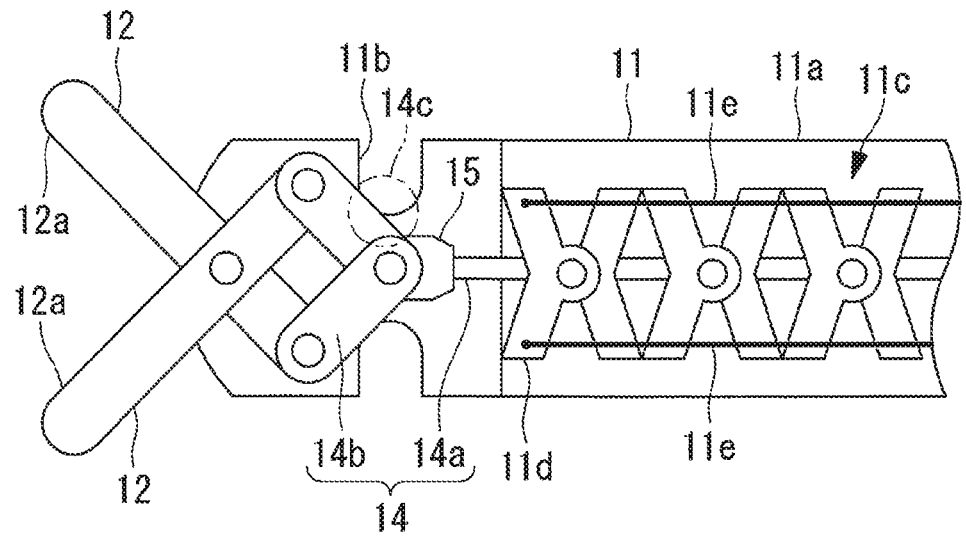
FIG. 7 is a partial configuration diagram showing another modification of the forceps device in FIG. 2.

In addition, in this embodiment, a bending portion (movable portion) 11c for changing the directions of the gripping pieces 12 may be provided at a distal end of the body portion 11, as shown in FIG. 7.

The bending portion 11c has a plurality of bending pieces 11d that are arranged in the longitudinal-axis direction of the body portion 11 and that are coupled with each other so as to be pivotable about axes that intersect the longitudinal axis. The distal ends of bending driving wires 11e, which extend to the driving portion 13, are coupled with the bending piece 11d positioned at the most distal end, and, as with the manipulation wire 14a, the bending portion 11c is bent by pushing and pulling base ends of the bending driving wires 11e by means of the driving portion 13. In the case in which the bending portion 11c is provided in this way, the bending piece 11d positioned at the most distal end is formed of an electric insulator so that the bending driving wires 11e are electrically insulated from the gripping pieces 12 and the linkage mechanism 14b.

In addition, in this embodiment, instead of providing the insulating member 15 between the manipulation wire 14a and the linkage mechanism 14b, any one of components that connect the gripping pieces 12 and the electric motor 13a, including the gripping pieces 12, may possess electrical insulating properties.

Figure 8:
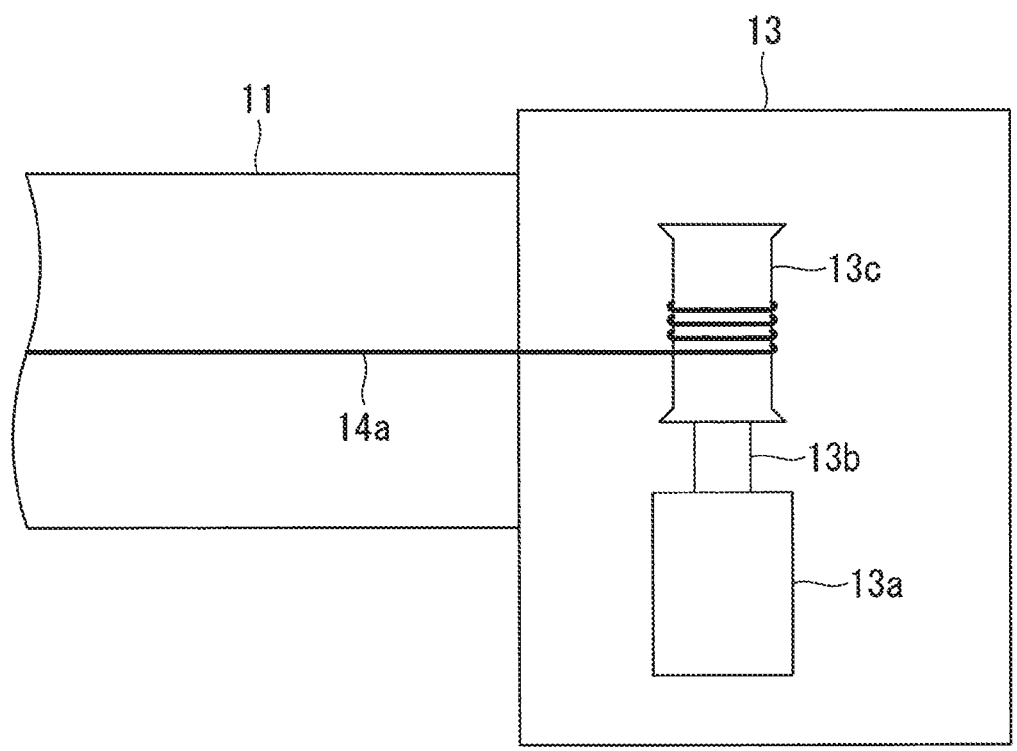
FIG. 8 is a partial configuration diagram showing another modification of the forceps device in FIG. 2.

For example, as shown in FIG. 8, at least one of a rotation shaft 13b and a pulley 13c that constitute a motive-power converting mechanism of the motor 13a in the driving portion 13 may possess electrical insulating properties. The pulley 13c is coaxially coupled with the rotation shaft 13b of the electric motor 13a, and a base-end portion of the manipulation wire 14a is wound around the pulley 13c. When the rotation shaft 13b is rotated by actuating the electric motor 13a, the manipulation wire 14a is pulled or pushed out due to rotation of the pulley 13c.

By doing so also, the rotation shaft 13b and/or the pulley 13c possessing electrical insulating properties function(s) in a similar manner as does the above-described insulating member 15, whereby it is possible to prevent the high-frequency current supplied to the gripping pieces 12 from affecting electrical systems of the driving portion 13, the manipulation input device 4, and the control portion 6. In addition, electrical systems of peripheral devices that are used together with the forceps device 1, such as an endoscope or the like into which the forceps device 1 is inserted, are also prevented from being affected by noise or the like.

Figure 9:
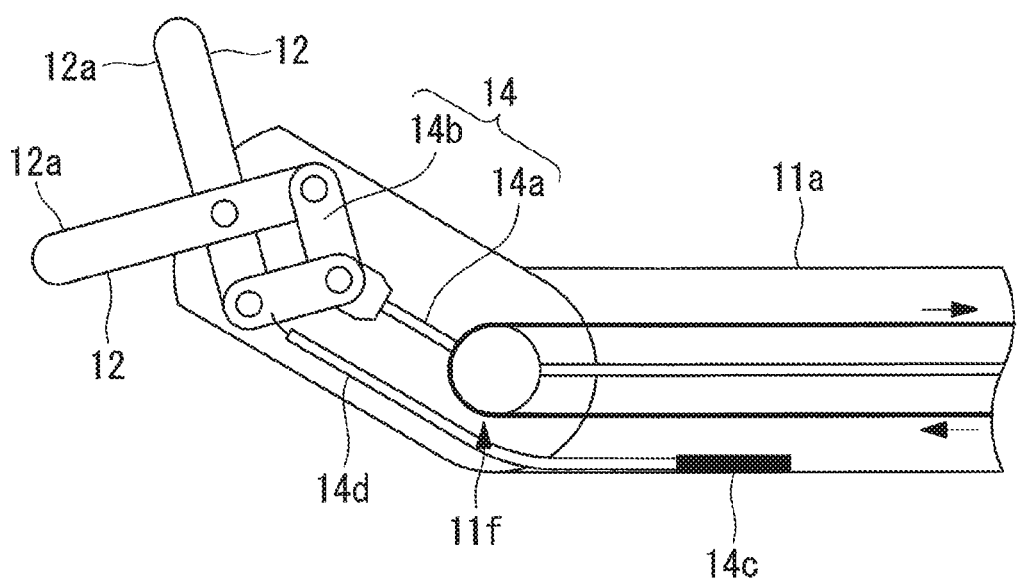
FIG. 9 is a partial configuration diagram showing another modification of the forceps device in FIG. 2.

In addition, in this embodiment, as shown in FIG. 9, a flexing joint portion (movable portion) 11f that can be flexed about an axis that intersects the longitudinal axis may be provided at the distal end of the body portion 11 instead of the bending portion 11c provided with the bending pieces 11d.

In the case in which the bending portion 11c or the flexing joint portion 11f is provided, it is preferable that the electric contact portion 14c be provided farther on the base-end side than the bending portion 11c or the flexing joint portion 11f is, as shown in FIG. 9.

The electric contact portion 14c in FIG. 9 is a member formed of a conductor and is provided at an outer circumferential surface of the sheath 11a. The surfaces of the electric contact portion 14c are covered with an electric insulator, excluding surfaces that are externally exposed, thus electrically insulating the electric contact portion 14c from the sheath 11a and objects that are built into the sheath 11a. The electric contact portion 14c is electrically connected with the pair of gripping pieces 12 inside the sheath 11a via a covered electric wire 14d that is covered with an electric insulator.

As described above, by providing the electric contact portion 14c at a position that does not move following movements of the bending portion 11c or that of the flexing joint portion 11f, it is possible to move the bending portion 11c or the flexing joint portion 11f while maintaining the contact between the electrode 22 and the electric contact portion 14c. In addition, because the electric contact portion 14c is disposed at a position further away from the tissue being gripped by the gripping pieces 12, it is possible to more easily perform manipulations for bringing the electrode 22 into contact with the electric contact portion 14c.

In addition, in this embodiment, a contact-detecting portion 16 that detects contact between the electric contact portion 14c and the electrode 22 may be provided.

Figure 10:
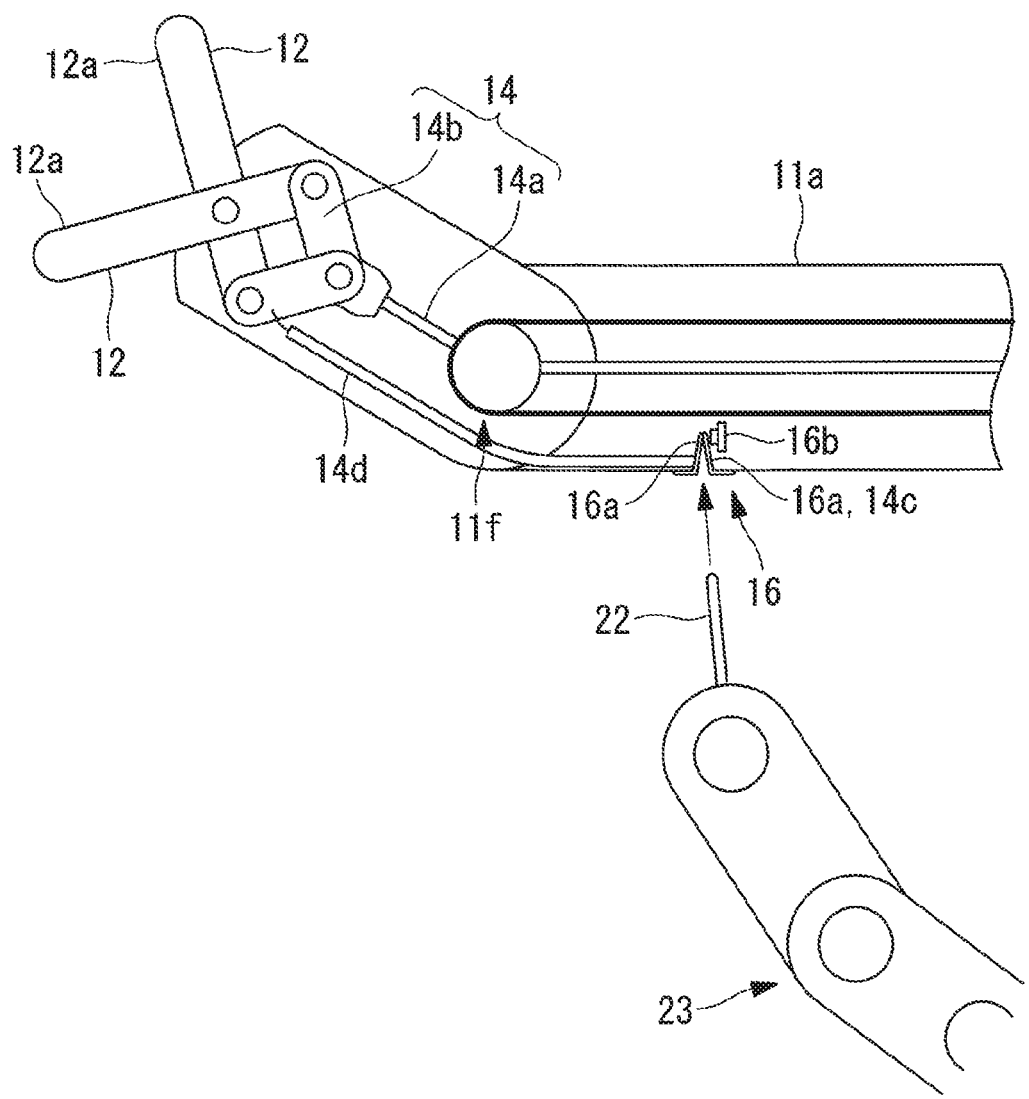
FIG. 10 is a partial configuration diagram showing another modification of the forceps device in FIG. 2.

As shown in FIG. 10, the contact-detecting portion 16 is formed of, for example, a microswitch provided at a side wall of the sheath 11a. Specifically, when the electrode 22 is press fitted between a pair of plate springs 16a that are disposed facing each other and that possess conductivity, while widening the gap between the plate springs 16a, a pressing button 16b provided behind the plate springs 16a is pressed. On the basis of the displacement of this pressing button 16b, contact between the plate springs 16a, which serve as the electric contact portion 14c, and the electrode 22 is detected. The contact-detecting portion 16 transmits detection signals to the control portion 6 when the contact between the electrode 22 and the electric contact portion 14c is detected.

The control portion 6 controls the forceps device 1 and the high-frequency treatment device 2 on the basis of the detection signals received from the contact-detecting portion 16. For example, when contact between the electric contact portion 14c and the electrode 22 is detected, the control portion 6 permits only the portions that are farther on the distal-end side than the bending portion 11c or the flexing joint portion 11f of the forceps device 1 is to be driven, and switches the high-frequency current to be supplied to the electrode 22 from the high-frequency power source 25 to a current having intermittent waves that are suitable for performing the hemostatic treatment.

By doing so, it is possible to stably perform hemostatic manipulations. In addition, by employing a configuration in which the electrode 22 is press fitted between the pair of plate springs 16a, a sufficient contact area is ensured between the plate springs 16a, which serve as the electric contact portion 14c, and the electrode 22, and the electrode 22 is stably secured to the plate springs 16a. By doing so, it is possible to stably supply the high-frequency current.

In addition, in this embodiment, although the electrode 22 and the gripping pieces 12 are brought into electrical contact with each other by driving the joint portion 23 of the high-frequency treatment device 2, the means of bringing the electrode 22 and the gripping pieces 12 into electrical contact is not limited thereto.

Figure 11:
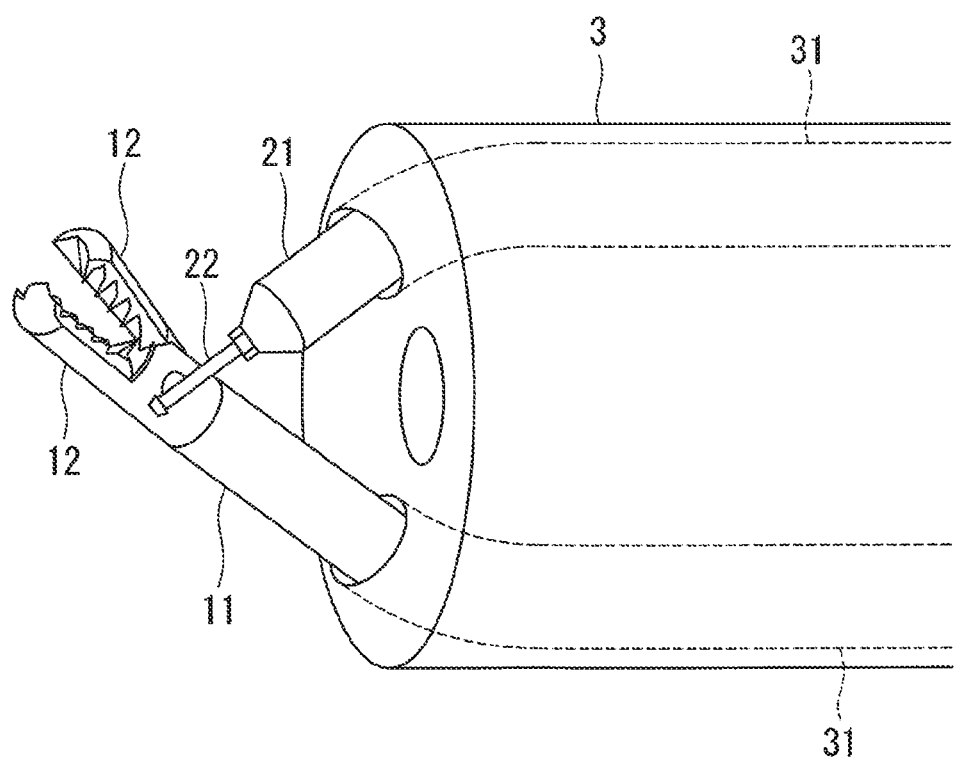
FIG. 11 is a diagram showing a modification of an endoscope in FIG. 1, and is a diagram for explaining motions of a forceps device and a high-frequency treatment device employed therein.

For example, as shown in FIG. 11, distal-end portions (contact parts) of the two treatment-tool channels 31 of the endoscope 3 may be inclined at relative angles at which extensions of the distal-end portions intersect each other. In this case, it is possible to bring the gripping pieces 12 and the electrode 22 into contact with each other just by adjusting the amounts by which the gripping pieces 12 and the electrode 22 protrude from the treatment-tool channels 31.

Figure 12:
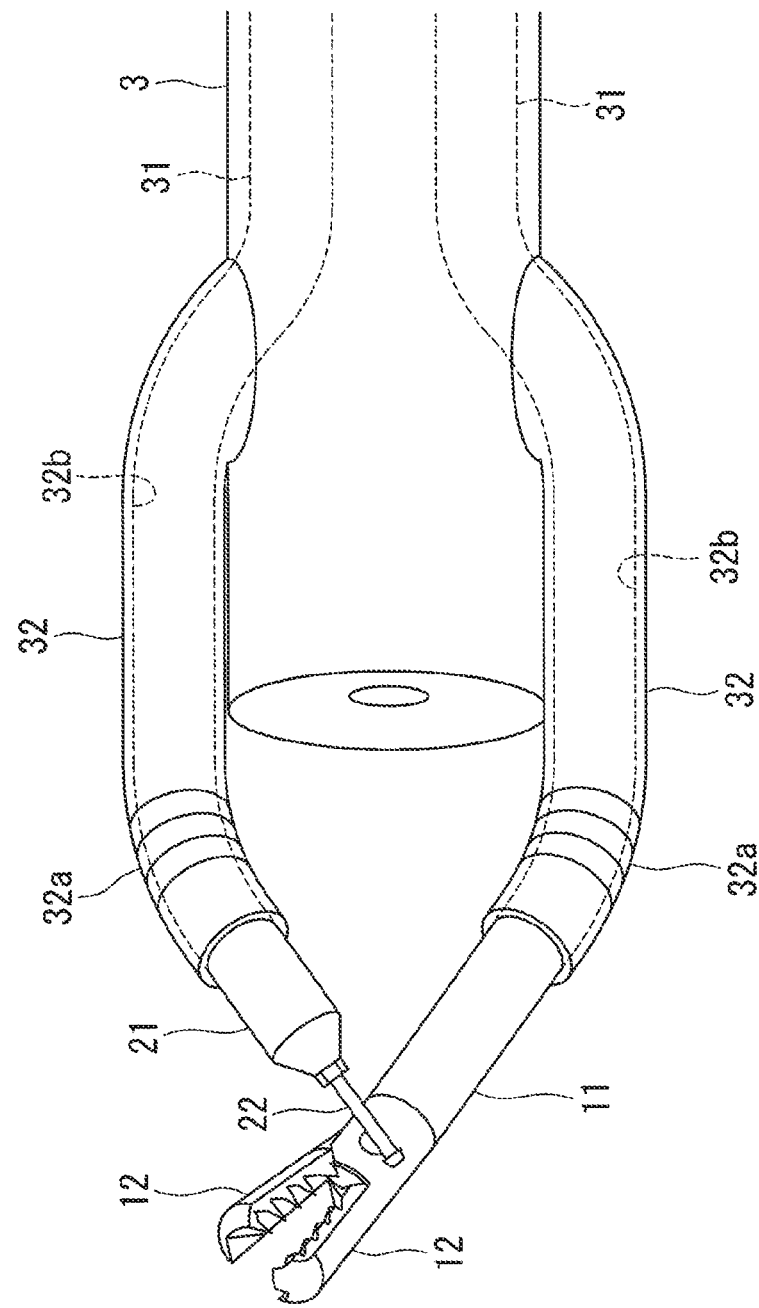
FIG. 12 is a diagram showing another modification of the endoscope in FIG. 1, and is a diagram for explaining motions of a forceps device and a high-frequency treatment device employed therein.

Alternatively, as shown in FIG. 12, the endoscope 3 may be provided with, at distal-end portions thereof, two arms (contact parts) 32 that are provided in the vicinity of the distal end of the endoscope 3 and that protrude forward with respect to the endoscope 3. Each of the arms 32 has a bending portion 32a, and the orientation of the distal end of the arm 32 can be changed by means of bending motions of the bending portion 32a. An arm channel 32b that communicates with the treatment-tool channel 31 is provided in each of the arms 32. The gripping pieces 12 and the electrode 22 that protrude from distal ends of the individual arms 32 via the arm channels 32b can be brought into contact with each other by means of bending motions of the bending portions 32a.

Figure 13:
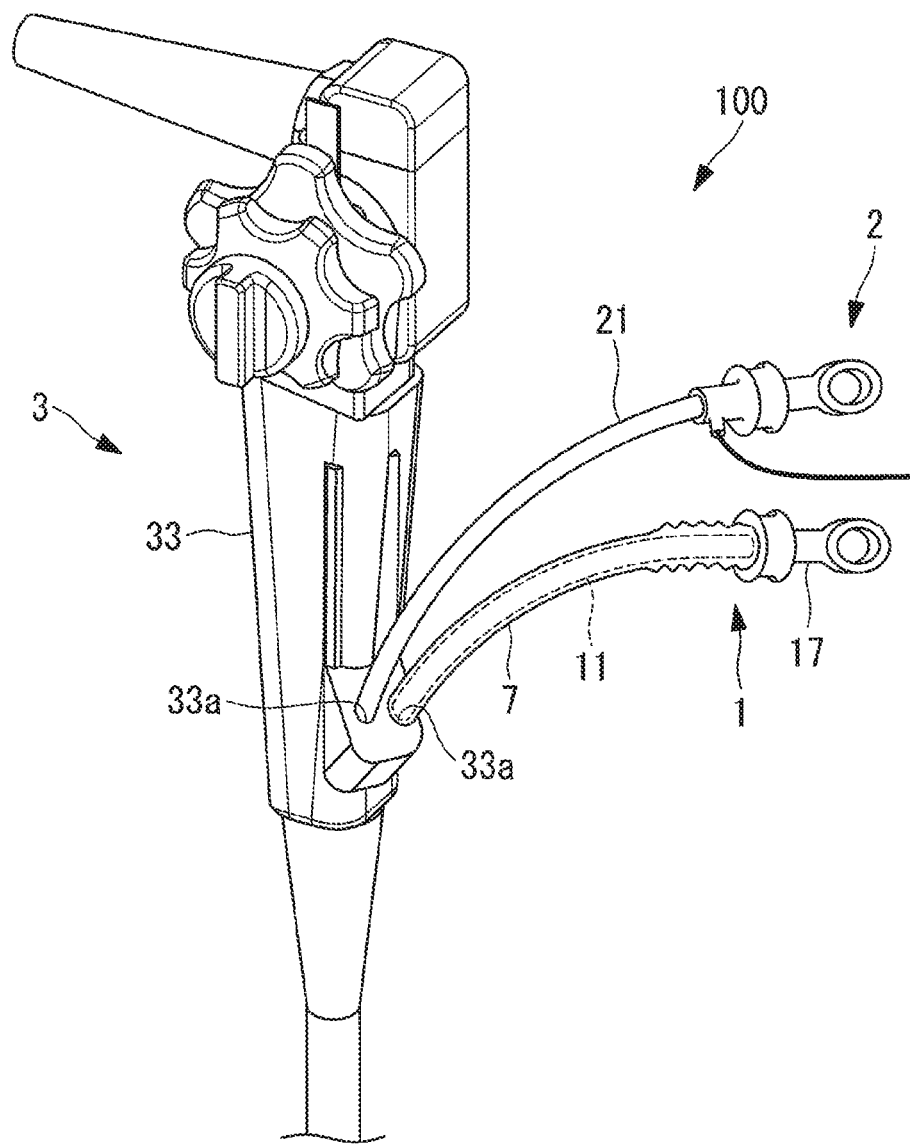
FIG. 13 is a partial configuration diagram of an endoscope that is used together with a manually manipulated forceps device and high-frequency treatment device.

In addition, in this embodiment, although the surgical system 100 provided with the forceps device 1 and the high-frequency treatment device 2 that are of electrically-manipulated types has been described, as shown in FIG. 13, the forceps device 1 and the high-frequency treatment device 2 may be of manually-manipulated types.

In this case, the forceps device 1 is provided with, instead of the driving portion 13, a manipulation portion (motive-power output portion) 17 that is manually manipulated at a base end of the body portion 11, motive power generated by manual manipulations by the operator is transmitted to the manipulation wire 14a from the manipulation portion 17, and thus, the manipulation wire 14a is made to undergo linear motions in the longitudinal directions. With such a manually manipulated forceps device 1, because the gripping pieces 12 and the manipulation portion 17 are electrically insulated from each other by the insulating member 15, it is possible to use a conductor such as a metal or the like as the material for the manipulation portion 17.

As shown in FIG. 13, a manipulation portion 33 of the endoscope 3 is provided with two insertion openings 33a that communicate with the treatment-tool channels 31, and into which the body portions 11 and 21 of the forceps device 1 and the high-frequency treatment device 2 are individually inserted. A cylindrical insulation cover (cover member) 7 having electrical insulating properties is connected to one of the insertion openings 33a into which the body portion 11 of the forceps device 1 is inserted.

By doing so, a portion of the body portion 11 of the forceps device 1 that is exposed at the exterior from the insertion opening 33a can be accommodated in the insulation cover 7. It is preferable that the insulation cover 7 be configured so as to be expandable in the longitudinal direction, for example, by forming at least a portion thereof in a bellows-like manner so that the length thereof changes in response to the movement of the body portion 11 in the longitudinal direction.

As a result, the above-described embodiment leads to the following aspects.

A first aspect of the present invention is a forceps device including: an elongated body portion; a pair of gripping pieces that are provided at a distal end of the body portion, at least one of which possesses conductivity, and that can be opened/closed relative to each other; a motive-power output portion that is provided at a base end of the body portion and that outputs motive power; a motive-power converting mechanism that connects the pair of gripping pieces and the motive-power output portion, and that converts the motive power output by the motive-power output portion into relative opening/closing motions of the pair of gripping pieces; and an insulating member that is provided in a pathway connecting the pair of gripping pieces and the motive-power output portion via the motive-power converting mechanism, and that electrically insulates the pair of gripping pieces and the motive-power output portion from each other.

With the first aspect of the present invention, by externally supplying a high-frequency current to at least one of the pair of gripping pieces, gripping a bleeding point, by using a high-frequency treatment device such as an electric scalpel, it is possible to achieve hemostasis by causing heat coagulation in tissue around the bleeding point between the pair of gripping pieces.

In this case, the pair of gripping pieces are connected to the motive-power output portion via the motive-power converting mechanism for opening/closing them. Because the insulating member is provided on the pathway that connects the pair of gripping pieces and the motive-power output portion, the high-frequency current supplied to the gripping pieces does not reach the motive-power output portion. Therefore, even in the case in which an electric motor is employed as the motive-power output portion or in the case in which peripheral equipment is electrically connected via the motive-power output portion, the electric motor or the peripheral equipment is actuated without being affected by the high-frequency current. In addition, electrical systems of peripheral devices that are used together with the forceps device, such as an endoscope or the like into which the forceps device is inserted, are also prevented from being affected by noise or the like. By doing so, the present invention can suitably be used not only as gripping forceps but also as high-frequency hemostatic forceps. Note that the above-described "pathway" includes the pair of gripping pieces.

In the above-described first aspect, the insulating member may be at least one of a plurality of components constituting the motive-power converting mechanism.

By doing so, it is possible to electrically insulate the gripping pieces and the motive-power output portion without increasing the number of components.

In the above-described first aspect, the motive-power converting mechanism is provided with: a manipulation wire that is placed along a longitudinal direction in the body portion and that is made to undergo linear motions in the longitudinal direction by means of the motive power output by the motive-power output portion; and a linkage mechanism that connects the manipulation wire and the pair of gripping pieces and that converts the linear motions of the manipulation wire into the relative opening/closing motions of the pair of gripping pieces, wherein the insulating member is provided between the manipulation wire and the linkage mechanism to couple the manipulation wire and the linkage mechanism.

By doing so, it is possible to use a metal manipulation wire that has generally been used in the related art.

In the above-described first aspect, the insulating member may be a second one of the gripping pieces formed of an electric insulator, and the motive-power converting mechanism is connected with the said second gripping piece, and causes the second gripping piece to undergo opening/closing motions with respect to a first one of the gripping pieces.

By doing so, when performing the hemostatic treatment, by supplying a high-frequency current to the first gripping pieces in a state in which a hemostatic point is gripped with the pair of gripping pieces so that the second gripping piece is placed adjacent to the peripheral tissue, it is possible to protect the peripheral tissue other than the hemostatic point from the high-frequency current. In addition, because the second gripping piece that serves as an insulating member is interposed between the motive-power converting mechanism and the first gripping piece, the high-frequency current supplied to the first gripping piece does not reach the motive-power converting mechanism.

In the above-described first aspect, the body portion may be provided with a cylindrical sheath that accommodates the motive-power converting mechanism and that possesses electrical insulating properties.

By doing so, it is possible to electrically insulate between the interior and the exterior of the body portion.

The above-described first aspect may include an electric contact portion that is provided at an intermediate position in a longitudinal direction of the sheath so as to be exposed at an exterior of the sheath, and that is electrically connected with the gripping pieces by passing through an interior of the sheath.

By doing so, by bringing the high-frequency treatment device into contact with, instead of the gripping pieces, the electric contact portion that is positioned farther on the base-end side than the gripping pieces are, it is possible to easily supply the high-frequency current to the gripping pieces at a position away from the tissue being gripped by the pair of gripping pieces.

In the above-described first aspect, the sheath may have, at an outer circumferential surface thereof, a slit that allows a portion, which is electrically connected with the pair of gripping pieces, of the motive-power converting mechanism to be exposed at the exterior, and the electric contact portion may be constituted of the portion of the motive-power converting mechanism.

By doing so, because the electric contact portion is provided inside the sheath, it is possible to prevent the high-frequency treatment device from coming into contact with the tissue when supplying the high-frequency current. In addition, because the position of an electrode or the like of the high-frequency treatment device inserted into the slit is stabilized, it is possible to stably maintain the electrical connection.

In the above-described first aspect, the electric contact portion may be constituted of a member that is secured to an outer circumferential surface of the sheath and that possesses conductivity.

By doing so, it is possible to provide the electric contact portion at an arbitrary position on the outer circumferential surface of the sheath.

In the above-described first aspect, the body portion may be provided with, at a distal end thereof, a movable portion that can be bent or flexed about an axis that intersects the longitudinal axis of the body portion, and the electric contact portion may be provided farther on a base-end side than the movable portion is.

By doing so, it is possible to move the gripping pieces by means of bending or flexing of the movable portion. In addition, because the electric contact portion is provided at a position that does not follow the movement of the movable portion, it is possible to maintain the contact between the electric contact portion and the high-frequency treatment device even while the movable portion is being moved.

A second aspect of the present invention is a surgical system including: any one of forceps devices described above; a high-frequency treatment device that includes an elongated body portion, and an electrode provided at a distal end of the body portion, and that discharges a high-frequency current; an endoscope that has two treatment-tool channels into which the forceps device and the high-frequency treatment device are individually inserted; and a contact part for placing the pair of gripping pieces and the electrode, which protrude from a distal-end surface of the endoscope via the treatment-tool channels, at positions at which mutual electrical connections are established therebetween.

With the second aspect of the present invention, the electrode is brought into contact with, by means of the contact part, the pair of gripping pieces gripping the bleeding point, and the high-frequency current is supplied to the gripping pieces from the electrode, and thus, it is possible to achieve hemostasis by causing heat coagulation in the tissue around the bleeding point between the pair of gripping pieces. In this case, it is also possible to suitably use the gripping forceps as high-frequency hemostatic forceps.

In the above-described second aspect, the high-frequency treatment device may be provided with, between the electrode and the body portion, a joint portion that can be flexed, and the contact part may be constituted of the joint portion.

By doing so, it is possible to move, by driving the joint portion, the electrode to a position at which contact is made with the gripping pieces.

In the above-described second aspect, distal-end portions of the two treatment-tool channels may be inclined at angles that make extensions thereof intersect each other, and the contact part may be constituted of the distal-end portions of the two treatment-tool channels.

By doing so, it is possible to place the gripping pieces and the electrode at positions at which they come into contact with each other just by making the gripping pieces and the electrode protrude from the distal-end surface of the endoscope via the treatment-tool channels.

In the above-described second aspect, the endoscope may be provided with, in the vicinity of the distal end thereof, arms that individually have arm channels that communicate with the two treatment-tool channels and bending portions that can be bent, and the contact part may be constituted of the bending portions of the arms.

By doing so, it is possible, by means of the bending motions of the bending portions, to place the gripping pieces and the electrode, which protrude via the treatment-tool channels and the arm channels, at positions at which the gripping pieces and the electrode come into contact with each other.

The above-described second aspect may be provided with a manipulation input device that is manipulated by an operator; and a control portion that controls the forceps device and the high-frequency treatment device in accordance with manipulations input via the manipulation input device.

By doing so, it is possible to electrically manipulate the forceps device and the high-frequency treatment device by using a manipulation input device that is provided separately from the forceps device and the high-frequency treatment device.

The above-described second aspect may be provided with a contact-detecting portion that detects an electrical contact between the pair of gripping pieces and the electrode, wherein the control portion controls at least one of the forceps device and the high-frequency treatment device on the basis of detection results of the contact-detecting portion.

By doing so, it is possible, by means of the contact-detecting portion, to automatically detect whether or not the hemostatic manipulations are performed on the basis of the presence/absence of electrical contact between the gripping pieces and the electrode, and it is possible to operate the forceps device and the high-frequency treatment device in accordance with different settings between during the hemostatic manipulations and during other manipulations.

In the above-described second aspect, the endoscope may be provided with a cylindrical cover member that externally extends from an insertion opening of the treatment-tool channel into which the forceps device is inserted, and the cover member may possess electrical insulating properties and is expandable in a longitudinal direction thereof.

By doing so, a portion of the forceps device that externally extends from the insertion opening of the treatment-tool channel can be electrically insulated from the surroundings by means of the cover member.

The present invention affords an advantage in that the present invention can also suitably be used as high-frequency hemostatic forceps by externally supplying a high-frequency current thereto.

REFERENCE SIGNS LIST 1 forceps device
2 high-frequency treatment device
3 endoscope
4 manipulation input device
5 display portion
6 control portion
7 insulation cover (cover member)
11 body portion
11a sheath
11b slit
11c bending portion
11d bending piece
11e bending driving wire
11f flexing joint portion
12 gripping piece
12a gripping surface
13 driving portion
13a electric motor (motive-power output portion)
13b rotation shaft
13c pulley
14 motive-power converting mechanism
14a manipulation wire
14b linkage mechanism
14c electric contact portion
14d covered electric wire
14e pulley
15 insulating member
16 contact-detecting portion
17 manipulation portion (motive-power output portion)
21 body portion
22 electrode
23 joint portion (contact part)
24 driving portion
25 high-frequency power source
31 treatment-tool channel
32 arm (contact part)
33 manipulation portion
33a insertion opening
100 surgical system

The invention claimed is:

1. A forceps device comprising:
an elongated body portion;
a pair of gripping pieces provided at a distal end of the body portion, at least one of the pair of gripping pieces having conductivity, the pair of gripping pieces being configured to be opened/closed relative to each other;
an actuator provided at a base end of the body portion for outputting motive power;
a motive-power converting mechanism that connects the pair of gripping pieces and the actuator and converts the motive power output by the actuator into relative opening/closing motions of the pair of gripping pieces; and
an insulating material provided in a pathway connecting the pair of gripping pieces and the actuator via the motive-power converting mechanism, the insulating material electrically insulating the pair of gripping pieces and the actuator from each other,
wherein the body portion comprises a cylindrical sheath that accommodates the motive-power converting mechanism, the cylindrical sheath having electrical insulating properties,
the forceps device further comprises an electric contact provided at an intermediate position in a longitudinal direction of the sheath, the electric contact being electrically connected to at least one of the gripping pieces via an interior of the sheath, and
the electric contact is positioned to be exposed to a space outside the sheath in order to receive a high-frequency current by coming in contact with an external electrode for supplying a high-frequency current, the electric contact being separate from the forceps device and forms a recess so as to come in contact with the external electrode.

2. The forceps device according to claim 1, wherein the insulating material is at least one of a plurality of components comprising the motive-power converting mechanism.

3. The forceps device according to claim 1, wherein the motive-power converting mechanism comprises:
a manipulation wire positioned along a longitudinal direction in the body portion, the manipulation wire being configured-to undergo linear motions in the longitudinal direction by means of the motive power output by the actuator; and
a linkage mechanism that connects the manipulation wire and the pair of gripping pieces, the linkage mechanism converting the linear motions of the manipulation wire into the relative opening/closing motions of the pair of gripping pieces,
wherein the insulating material is provided between the manipulation wire and the linkage mechanism to couple the manipulation wire and the linkage mechanism.

4. The forceps device according to claim 1,
wherein the insulating material comprises one of the pair of gripping pieces being formed of an electric insulator,
an other of the pair of gripping pieces is conductive to the electric contact, and
the motive-power converting mechanism is connected with the one of the pair of gripping pieces, the motive-power converting mechanism causing the one of the pair of gripping pieces to undergo opening/closing motions with respect to an other of the pair of gripping pieces.

5. The forceps device, according to claim 1,
wherein the sheath has, at an outer circumferential surface thereof, a slit that exposes a portion of the motive-power converting mechanism to the exterior of the sheath, the portion being electrically connected with at least one of the pair of gripping pieces, and
the electric contact comprises the portion of the motive-power converting mechanism.

6. The forceps device according to claim 1, wherein the electric contact comprises a member secured to an outer circumferential surface of the sheath, the electric contact being conductive.

7. The forceps device according to claim 1,
wherein the body portion comprises a movable portion configured to be bent or flexed about an axis that intersects the longitudinal axis of the body portion, the movable portion being arranged at a distal end of the body portion, and the electric contact being arranged proximally farther than the movable portion.

8. A surgical system comprising:
the forceps device according to claim 1;
a high-frequency treatment device comprising an elongated body portion, and an electrode provided at a distal end of the body portion of the high-frequency treatment device, the electrode being configured to discharge a high-frequency current;
an endoscope comprising two treatment-tool channels into which the forceps device and the high-frequency treatment device are individually inserted; and
a contact part configured to place the pair of gripping pieces and the electrode, which protrude from a distal-end surface of the endoscope via the treatment-tool channels, at positions at which mutual electrical connections are established therebetween.

9. The surgical system according to claim 8,
wherein the high-frequency treatment device is provided with, between the electrode and the body portion of the high-frequency treatment device, a joint configured to be flexed, and
the contact part comprises the joint portion.

10. The surgical system according to claim 8,
wherein distal-end portions of the two treatment-tool channels are inclined at angles such that central axes extending from the two treatment-tool channels intersect, and
the contact part comprises the distal-end portions of the two treatment-tool channels.

11. The surgical system according to claim 8,
wherein the endoscope comprises, in a vicinity of the distal end of the endoscope, arms that individually have arm channels communicating with the two treatment-tool channels and bending portions that can be bent, and
the contact part comprises the bending portions of the arms.

12. The surgical system according to claim 8, further comprising:
a manipulation input device manipulated by an operator; and
a controller configured to control the forceps device and the high-frequency treatment device based on manipulations input via the manipulation input device.

13. The surgical system according to claim 12, further comprising:
a contact-detecting sensor that detects an electrical contact between the pair of gripping pieces and the electrode,
wherein the controller controls at least one of the forceps device and the high-frequency treatment device based on detection results of the contact-detecting sensor.

14. The surgical system according to claim 8,
wherein the endoscope comprises a cylindrical cover that externally extends from an insertion opening of the treatment-tool channel into which the forceps device is inserted, and
the cover comprises electrical insulating properties and is expandable in a longitudinal direction.

15. A forceps device according to claim 1, further comprising a contact-detecting sensor that detects conduction between the external electrode and the electric contact.

16. A method for using the forceps device according to claim 1 and a high-frequency treatment device comprising the external electrode and a high-frequency power source for supplying the high-frequency current to the external electrode, the method comprising:
gripping tissue with the pair of gripping pieces;
inserting the external electrode into the recess of the electric contact; and
supplying the high-frequency current to the external electrode from the high-frequency power source.

* * * * *